United States Patent [19]
Dal Santo

[11] Patent Number: 6,022,109
[45] Date of Patent: Feb. 8, 2000

[54] HAND-HELD PUPILOMETER

[76] Inventor: John P. Dal Santo, 1439 Whitney Blvd., Belvidere, Ill. 61008

[21] Appl. No.: 09/208,884

[22] Filed: Dec. 10, 1998

[51] Int. Cl.[7] .................................................. A61B 3/10
[52] U.S. Cl. ........................................................ 351/221
[58] Field of Search ................................ 351/205, 209, 351/210, 206, 221, 223, 224

[56] References Cited

U.S. PATENT DOCUMENTS

| | | | |
|---|---|---|---|
| H574 | 2/1989 | Merkel | 251/223 |
| 3,936,162 | 2/1976 | Krakau et al. . | |
| 3,966,310 | 6/1976 | Larson . | |
| 4,755,043 | 7/1988 | Carter . | |
| 4,815,839 | 3/1989 | Waldorf . | |
| 4,850,691 | 7/1989 | Gardner et al. | 351/221 |
| 4,955,389 | 9/1990 | Schneider . | |
| 5,187,506 | 2/1993 | Carter | 351/221 |
| 5,305,764 | 4/1994 | Yamada et al. . | |
| 5,422,690 | 6/1995 | Rothberg et al. . | |
| 5,617,872 | 4/1997 | Scinto et al. . | |
| 5,646,709 | 7/1997 | Carter . | |
| 5,661,538 | 8/1997 | Carter . | |
| 5,704,369 | 1/1998 | Carter . | |
| 5,892,568 | 4/1999 | Carter | 351/218 |

OTHER PUBLICATIONS

Fairville Medical Optics, Inc., 2–page product information literature on "Pupilscan II", Type 12.

*Primary Examiner*—George Manuel
*Attorney, Agent, or Firm*—Keith Frantz

[57] ABSTRACT

A self-contained, battery powered, hand-held pupilometer is constructed with a binocular-type housing, is adapted for monocular operation to test the response of a subject's pupil to a light stimulus, and includes internal microprocessor-based control and data processing and storage apparatus. Response of the subject's other pupil may be tested by flipping the instrument.

13 Claims, 2 Drawing Sheets

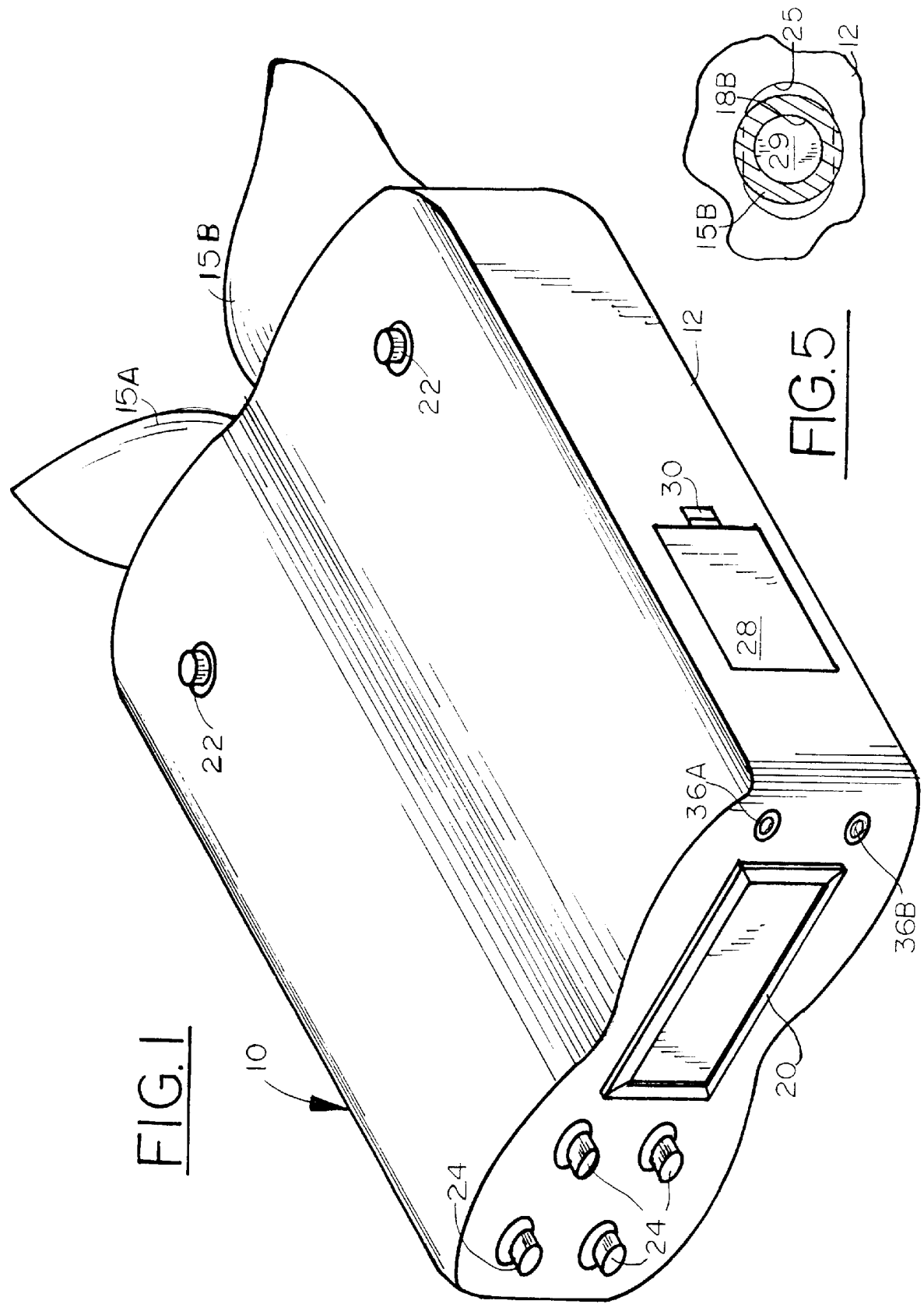

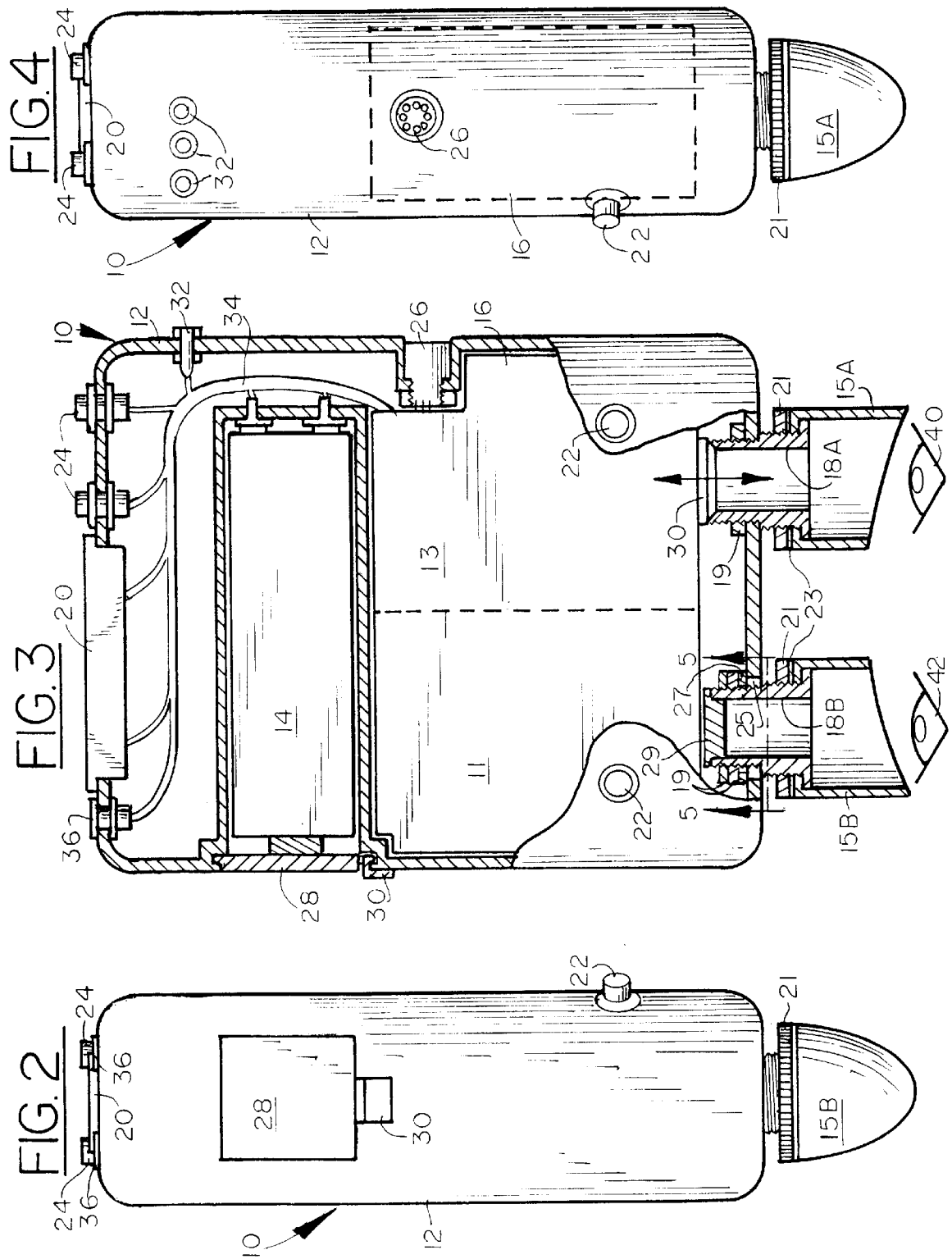

HAND-HELD PUPILOMETER

BACKGROUND OF THE INVENTION

1. Field of Invention

This invention relates generally to pupilometers, and more particularly to hand-held pupilometers which, while suitable for general pupilometer test purposes, are particularly useful for "field" testing, i.e., testing at locations remote from an office, laboratory, or other building or controlled environment.

2. Prior Art

Modern pupilometers provide an indication of the state of an individual's autonomic nervous system by measuring the individual's pupillary response to a light stimulus. With such response data, it has been found that pupilometers may be used in detecting fatigue in an individual as indicated by the individual's alertness or sleepiness, detecting the presence of alcohol or drugs, or Alzheimer's disease, and detecting other conditions related to nervous system functional impairment. Thus, pupilometers may be useful in the medical, transportation, and military and law enforcement fields, in industry, and in other areas in which it is desirable to detect such conditions. However, pupilometers have meet with limited acceptance, particularly in the transportation, military and law enforcement fields, due in part to certain deficiencies of prior pupilometers.

Briefly, conventional modern pupilometers generally include optical-electronic apparatus for generating a pupillary response-inducing light stimulus, and for measuring the diameter of the stimulated pupil over a period of time to establish the response (including parameters such as pupil constriction velocity, initial, minimum and final pupil diameter, time to minimum, and reflex amplitude) of a user/subject's pupils to the light stimulus. To this end, conventional pupilometers typically include visible light emitting diodes to produce the response-inducing light stimulus (i.e., diodes to generate a visible flash of light directed along an optical path and at the subject's eye to cause contraction of the subject's pupil), and infrared diodes (or other IR source) and associated optics and electronics adapted to direct the IR source to and from the subject's eye for measuring the dynamic pupillary response to the light stimulus. The pupillary response measuring apparatus typically includes either (i) an electronic pupil-imaging device such as a charge-coupled device (CCD) or other optical detector array, the image being detected on a two-dimensional detection device or a one-dimensional scanning device and then processed for pupil size information, or (ii) apparatus for detecting IR light scattered from the subject's eye and converting the detected optical power to an electrical signal indicative of the diameter of the pupil. A target arrangement is typically provided to assist the user in alignment of the pupil to be tested with the optical path of the optical-electronic apparatus. Pupilometers have been provided with apparatus for automatically detecting the presence of a pupil in the optical path of the optical-electronic apparatus, and/or the position of the pupil relative to the optical path, to provide either the user with pupil position feedback or a test administrator or operator with pupil position information indicating proper pupil alignment for test initiation, and/or for tracking the position of the pupil. Provision is also typically made for a microprocessor-based controller to control the operation of the optical-electronics apparatus and to analysis the pupillary response data, and for storage of the response data and analytical results.

Additional specific information regarding pupilometers, and the use of pupillometers and pupillary response data in detecting the presence of conditions related to nervous system impairment is provided in, among others, Scinto et al., U.S. Pat. No. 5,617,872 (Hypersensitive Constriction Velocity Method for Diagnosing Alzheimer's Disease in a Living Human) and U.S. Pat. No. 5,704,369 (Non-Invasive Method for Diagnosing Alzeheimer's Disease in a Patient); Carter, U.S. Pat. No. 5,646,709 (Portable Hand-held Pupillometer with Dynamic Electronic Image Centering Aid and Method of Use Thereof), U.S. Pat. No. 5,661,538 (Portable Self-Measurement Pupillometer with Active Opto-Electronic Centering Aid and Method of Use Thereof), U.S. Pat. No. 4,755,043 (Portable Scanning Digital Pupillometer and Method of Use Thereof) and U.S. Pat. No. 5,187,506 (Method and Apparatus for Determining Physiological Parameters Based on Pupil Response); Gardner et al., U.S. Pat. No. 4,850,691 (Method and Apparatus for Determining Pupillary Response Parameters); Rothberg et al., U.S. Pat. No. 5,422,690 (Fitness Impairment Tester); Cornsweet et al., U.S. Pat. No. 5,410,376 (Eye Tracking Method and Apparatus) and U.S. Pat. No. 5,042,937 (Optical System for an Ophthamological Instrument for Examination of Pupillary Responses); Kardon, U.S. Pat. No. 5,490,098 (Automated System and Method for Determining Pupillary Threshold Response); and Anderson, U.S. patent application No. 09/312,094.

In general, pupilometers are available in table-top models and hand-held models. In order to measure and record pupillary response data, and for analysis of the response data, such prior pupilometers are typically tethered to a laptop computer, or other microprocessor based control and data processing and storage unit with a data and power transmission line.

Table-top model pupilometers are typically of binocular construction for testing both of the subject's eyes. One such prior pupilometer is disclosed in Carter, U.S. Pat. No. 5,661,538. This pupilometer is equipped with a binocular optical block for stimulating the subject's pupils and detecting pupillary response with an electronic imaging device, a selector knob to enable testing of one eye and then the other eye, and may be tethered to a laptop computer for power requirements, for software control processing such as to drive the optical block, and to provide means for analyzing the pupillary response data.

Prior hand-held pupilometers are typically of monocular construction and operation, and are also typically tethered to a laptop computer for instrument control and data processing and storage purposes. Unfortunately, such tethered arrangements are inconvenient if the pupilometer is to be used at a location remote from an office, laboratory or other controlled environment because the operator must carry-along and set-up the computer at the remote location, and because the testing location is limited to proximate the laptop computer by the length of the tether line.

As a result, such prior pupilometer are not practical for extensive "field" use such as would be common in transportation, military and law enforcement fields, and have met with limited acceptance in such fields. In addition, the need for the laptop computer results in substantial additional expense over and above the cost of the pupilometer instrument.

Hand-held pupilometers are disclosed in Carter, U.S. Pat. Nos. 5,646,709 and 4,755,043. Each of these pupilometers are of monocular construction and operation, with an elongated handle for one-handed gripping, and with an enlarged head which carries an eyepiece and the associated light generating and pupillary imaging and response measuring optics. Unfortunately, in addition to being tethered to a laptop computer, a pupilometer with this construction presents the potential to used as a weapon if given to a non-friendly subject for self-testing, such as to a subject to be tested for the presence of alcohol or drugs. Specifically, the "hammer-like" construction of such prior hand-held pupilometers presents a danger that the operator may be struck with the enlarged head if the instrument is swung in an aggressive manner by the user. Such an arrangement has presented an additional barrier to acceptance of prior hand-held pupilometers in law enforcement and related fields.

One prior hand-held pupilometer of Fairville Medical Optics, Inc. of the United Kingdom, identified under the name/trademark PUPILSCAN II, Type 12, is a self-contained, hand-held pupilometer that is adapted to test and record pupillary response data without the need to be tethered to a separate microprocessor-based control and data processing device. However, this pupilometer is of conventional pupilometer monocular construction, having an enlarged head and an elongated handle, and therefore presents the same potential to be used as a weapon as associated with other prior hand-held pupilometers.

Thus, there is a need for a cost-effective, self-contained, hand-held pupilometer that is capable of measuring, analyzing and storing pupillary response data without the need to be tethered to a separate microprocessor-based control and data processing device for ease of field use, and that is constructed to reduce the potential weapon-like nature of the instrument and thus reduce the likelihood that the pupilometer may be used by the test subject as a weapon against an operator administering or observing the test.

SUMMARY OF THE INVENTION

The general aim of the present invention is to provide a new and improved self-contained, cost-effective hand-held pupilometer that is capable of measuring, analyzing and storing pupillary response data without the need to be tethered to a laptop or other microprocessor based control and data processing apparatus to enhance ease of field use of the pupilometer as compared with prior pupilometers, and that is constructed in a compact manner to enhance the safety of the operator observing or administering the test by reducing the effectiveness of using the instrument as a weapon if swung by an unfriendly test subject, and thus reduce likelihood that the instrument may be used as a weapon against the operator.

A detailed objective is to achieve the foregoing by providing a self-contained pupilometer having a compact binocular-like construction with integral control and data processing unit.

Another detailed objective is to provide such a self-contained pupilometer having monocular operation to reduce the size, complexity and cost of the instrument, yet being capable of testing both of a subject's eyes.

These and other objectives and advantages of the invention will become more apparent from the following detailed description when taken in conjunction with the accompanying drawings.

Briefly, a preferred embodiment of the pupilometer of the present invention includes a generally symmetrical hand-held sized housing of binocular-like construction that is equipped with soft rubber eyecups connected at spaced eyepiece locations for alignment with a subject's eyes; an internal optical-electronics pack including the pupillary light stimulus and response measurement apparatus, an internal microprocessor based controller to control the operation of the instrument, to perform data processing and analysis of the pupillary response data, and internal data storage for storing the response data and analytical results; and a removable battery pack for powering the instrument. One of the eyepiece locations is open to establish an optical test path and visual communication with the optical-electronics pack for testing the pupillary response of the associated eye. The instrument also includes a start mechanism such as a switch to initiate the pupillary test sequence when the subject's pupil is properly positioned along the optical test path; a visual display screen for display of information such as test identification, pupil position, and pupillary response data; operational control switches to initiate desired instrument control functions, to input test-subject identification data, to establish desired test parameters, and for related administrative functions; and one or more data ports or connectors to enable transfer of data for archival purposes to another storage location and/or for optional remote operation of the instrument. Preferably, the second eyepiece location is blocked, isolating the subject's second eye from the internal light sources of the optical pack while testing the first eye, and thus providing for monocular operation. Advantageously, both of a subject's pupils may be tested by simply inverting the instrument after testing of the first eye is completed.

BRIEF DESCRIPTION OF THE DRAWINGS

FIG. 1 is a front perspective view of a pupilometer incorporating the unique aspects of the present invention.

FIG. 2 is a left side view of the pupilometer.

FIG. 3 is a top view of the pupilometer with certain parts broken away to reveal certain internal components.

FIG. 4 is a right side view of the pupilometer.

FIG. 5 is a cross-sectional view taken substantially along the line 5—5 of FIG. 3.

While the invention is susceptible of various modifications and alternative constructions, a certain illustrated embodiment has been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DETAILED DESCRIPTION OF THE INVENTION

For purposes of illustration, the present invention is shown in the drawings as embodied in a hand-held pupilometer instrument 10 (FIG. 1) for detecting the response of an individual's pupils to a light stimulus. The instrument is adapted for either use by a user/test subject alone (i.e., self-testing) or for testing of the subject to proceed under the supervision of an administrator/operator.

In general, the pupilometer 10 includes a housing 12, rubber eyecups 15A, 15B, an optical-electronics pack 16 (FIG. 3) comprising optical and electronic components to generate a light stimulus and measure the subject's pupillary response to the light stimulus, a visual display screen 20, control and start button-switches, 24 and 22, respectively, an on-off switch (not shown), a data transfer connector 26, and operable interconnections including electrical wires 34 between the instrument components.

The instrument 10 is powered by a rechargeable battery pack 14 located in the housing 12. A removable or hinged battery cover 28 maintains the battery in position in the housing when closed, and may be opened for removal and replacement of the battery by releasing spring clip 30. Light emitting diodes (LEDs) 32 indicate battery condition such as green for a fully charged battery, red for a discharged battery, and yellow for warning of a low-charge battery condition.

The visual display screen 20 is of a commonly available type such as a liquid crystal display (LCD) or active matrix screen, and is operably connected to the optical-electronics pack 16 for display of test related information such as instrument operational and performance parameters, test and subject identification data, and pupillary response data.

In accordance with the present invention, the pupilometer 10 is a compact, self-contained hand-held pupilometer having binocular-type construction, and preferably monocular operation yet being capable of testing the pupillary response of both of a subject's eyes.

In carrying out one aspect of the invention, the housing 12 is of generally symmetrical, substantially closed binocular-like construction having top and bottom portions, front and back portions, and opposing side portions. The housing (a) is sized to be held comfortable in the subject's hands, such as less than approximately: 3 inches in height, 8 inches in length, and 6 inches in width, and (b) is shaped for comfortable gripping on the sides, with the subject's fingers wrapping around and gripping the top of the housing and the subject's thumbs supporting the bottom of the housing.

The housing may be made from any suitable material but is preferably molded from an impact resistant plastic, generally encapsulated with water-proof rubber of the type that promotes easy gripping and for a cushioning effect upon impact, and is generally sealed to reduce the likelihood of water and dust contamination entering the instrument. One or more access panels (not shown) are optionally provided in the housing for installation of the optical-electronics pack 16 and other internal components into the housing, or preferably the housing is formed such as from upper and lower halves and provided with means for connecting the two halves together after the internal components are connected in place inside the upper and lower halves of the housing.

The eyecups 15A, 15B are laterally spaced at the back of the housing for alignment with the subject's eyes 40, 42, and are shaped to generally conform to the subject's face in a binocular-like manner to assist with such alignment, and to preferably prevent outside light from entering the subject's eyes to reduce the likelihood that the subject will be distracted during the test. In the embodiment shown, the eyecups are connected to eyepieces 18A and 18B at spaced eyepiece locations. The eyepieces are held in openings in the back of the housing 12 with threaded nuts 19, and the eyecups are secured to the eyepieces with threaded nuts 21, washers 23 being disposed between the nut and a forward flange of each eyecup to enable tightening of the nuts 21 against the rubber flanges. In this instance, the spacing between the eyepieces may be adjusted by manually sliding eyepiece 18B along slot 25 (FIG. 5) in the back of the housing, a spring-type washer 27 imparting spring-load induced friction against the housing wall surrounding the slot 25 for maintaining the eyepiece in position during normal handling vibrations, but which may be manually overcome for sliding adjustment of the eyepiece 18B to a desired position. It will be apparent that the two eye-cups 15A, 15B may be of other configurations such as merged into a single goggle-type rubber eyecup shaped to generally surround both eyes at said eyepiece locations and assist in positioning of the pupilometer; and/or the eyecup(s) may be connected other than as shown such as directly to the back of the housing 12.

Alternately, the housing 12 may be of a conventional binocular-like construction with two monocular-type side halves joined by a center hinge connection for pivoting along the axis extending through the center of the instrument from front to back. As with conventional adjustable binoculars, such an arrangement permits adjustment of the space between the eyecups for alignment with the subject's eyes by pivoting the two halves of the housing toward or away from each other.

Optical communication between the optical-electronics pack 16 and the subject's eye at eyepiece location 18A is established along an optical path "A" (FIG. 3) generally through the center of eyepiece 18A for testing the pupillary response of the eye 40 associated therewith. This operative eyepiece location is preferably sealed with glass 30 or other transparent material to prevent contamination from entering the instrument, but is selected to not interfere with transmission of light stimulus along optical path "A" or pupillary detection and response measurement.

In general, the optical-electronics pack 16 includes an optical pack 13 and a microprocessor-based controller and data processing and storage unit 11. The optical-electronics pack 16 is shown as divided into the optical pack 13 and the controller 11 with dashed-lines in FIG. 3, but it will be understood that the components of the optical pack and the controller may be positioned in the housing as desired in carrying out the invention.

In general, the optical pack 13 includes optical and electronic components for (a) generating a pupillary response-inducing light stimulus directed through eyepiece 18A, and (b) detecting and measuring the diameter of the pupil at eyepiece 18A over a period of time to establish pupillary response of eye 40 at eyepiece 18A to the light stimulus. To this end, preferred embodiments of the optical pack 13 include light emitting diodes that generate a flash of visible light to provide the response-inducing light stimulus; an eye/pupil illumination source such as infrared emitting diodes or an IR laser; optical components including lenses and mirrors positioned and adapted to (a) direct the visible light from the light emitting diodes through eyepiece 18A if the light emitting diodes are not positioned in line-of-sight in optical path "A", and (b) direct the IR radiation from the source to and from the subject's eye 40 through eyepiece 18A; a detector and associated components positioned and adapted to (a) sense the IR radiation reflected back through eyepiece 18A from the subject's eye 40 or associated pupil, and (b) produce an electrical output signal that is indicative of the pupil diameter of eye 40 over a period of time based on the reflected illumination or IR light; and a target arrangement for the subject to focus on, to assist the subject in positioning the pupil of eye 40 in alignment with optical path "A" during the test. Suitable detectors include (a) electronic pupil-imaging devices such as charge-coupled devices (CCD), OpticRAM arrays, or other photo-optical image-detector arrays adapted to generate an electrical output signal that can be processed to determine the size of the pupil, or (b) detector(s) adapted to sense the illumination or IR radiation reflected from the subject's pupil or eye and to convert the detected optical power of the reflected light to an electrical signal indicative of pupil diameter.

The optical pack 13 is not shown in detail in the drawings because, and as will be apparent to those skilled in the art, alternate suitable optical pack 13 embodiments within the scope of the present invention are provided from known pupillary response inducing and measuring technology, such as, for example, the targeting and optical pupillary response inducing and sensing arrangements disclosed in Anderson, U.S. provisional patent application No. 60/085,543, Gardner et al., U.S. Pat. No. 4,850,691, Carter, U.S. Pat. Nos. 5,187,506, 5,646,709, and/or 5,661,538.

The internal control pack 11 generally includes (1) electronic data storage apparatus, for storage of instrument software, test input data, pupillary response data, and analytical results, such as, for example, read-only permanent memory (ROM), random access memory (RAM) and/or disk-based storage such as floppy-disk or recently developed miniaturized hard-drive technology, and (2) a microprocessor-based controller and associated electronics and components interfaced and operably connected for processing instrument software code to generally (a) control and drive the sequencing and operation of the optical pack 13 including the illumination source, the visible-light emitting diodes, and the detector and associated components, (b) receive input data including test identification data, (c) receive the pupil diameter-indicative electrical output signal from the detector apparatus of the optical pack 13, process the signal/data to generate desired pupillary response data such as pupil constriction velocity, initial, minimum and final pupil diameter and time to minimum and reflex amplitude, and analyze the pupillary response data, (d) store the input data, test data and analytic results, and (e) drive or control the other operational and administrative functions of the pupilometer as applicable. In short, the internal control pack 11 performs the digital control and data processing and storage functions of, and replaces the conventional tethered laptop computer (or equivalent apparatus) of many prior pupilometers. As a result, the pupilometer 10 is a self-contained, hand-held instrument that is particularly suited for testing of subjects at "off-site" locations.

As with the optical pack, the control unit 11 is not shown in detail in the drawings because, and as will be apparent to those skilled in the art, alternate suitable microprocessor-based controller unit embodiments are provided or adapted from known pupilometer and microprocessor control and data processing technology, and is necessarily adapted in part according to the optical pack 13 embodiment including the detector type of the pupilometer 10.

The operational control button switches 24 are connected to the optical-electronic pack 16 and associated pupilometer components to control instrument power-on and power-off functions, to provide a means for data input, and for function selection and operational control of the instrument. For purposes of illustration, four button-type switches 24 are shown in the drawings, but it will be understood that in preferred embodiments the precise number and designated function of these switches will vary according to the functions to be accomplished or implemented in such embodiments, and that the control button switches shown may be replaced by other data input and function selection means in alternate embodiments such as with a small alpha-numeric keypad.

In general, the operation of the pupilometer 10, including the elements of optical pack 13, is software controlled, and the software is written to provide the operator with means for input of initial data prior to each test. Input data includes test identification data such as identification of the test subject, the time and date of the test, the type of test to be conducted, and possibly identification of the operator conducting the test. In preferred embodiments, the software is written to display conventional data fields on the display screen 20 in a predetermined order for entry of initial data by the operator utilizing designated control switches 24 after the instrument is turned on or upon actuation of a designated switch 24 to begin the data entry sequence. In alternate embodiments, the software is written to display a conventional-type menu of choices on the display screen for the operator to select from, each selection being made by designated control switches 24, and each selection prompting the operator to provide the data input for the selected data parameter through actuation of designated control switches. Optionally, the software is written to automatically store the time and date of the test with the associated response data.

In the embodiment shown, a start switch 22 is positioned near the back of the housing 12 for initiating the test-cycle light stimulus production and response measuring function of the pupilometer, the preferred test-cycle operational sequences of the pupilometer 10 proceeding according steps suitable for the specific embodiment of the optical pack 13 and control unit 11 of the pupilometer. For example, the instrument may be adapted such that pressing the start switch 22 illuminates a target for the subject to focus on, and releasing the switch triggers the response inducing light stimulus flash and response measuring sequence of the optical pack 13 for collection of pupillary response data. Alternately, in embodiments that include means for indication of pupil position to assist the user in centering the pupil prior to the test, pressing the start causes the optical pack 13 to generate and project initial illumination towards the subject's eye at eyepiece 18A to provide pupil position indication to the subject and/or the operator through visual or audio communication means such as by projecting the pupil position on the display screen 20, or lighting a target in the optical path "A", and when the pupil is properly aligned, release of the switch 22 triggers the response inducing light stimulus flash and response measuring sequence of the optical pack. It will be apparent that these and other operating sequences may be coded into the software, and utilized in the pupilometer of the present invention according to the arrangement of the optical pack and control unit.

The pupilometer 10 may be optionally equipped with two start buttons 22 (as shown), one to be actuated by a finger or thumb of each hand, and connected in series such that both must be simultaneously pressed by the subject to initiate a suitable test sequence. Advantageously, such an arrangement requires the subject to hold the instrument with two hands, reducing the likelihood of the subject dropping the instrument during the test such as might be otherwise likely if the subject is intoxicated, and insuring that both of the subject's hands are occupied during the test, thus providing an additional measure of safety for the operator against potentially non-friendly subjects as might be encountered in law enforcement use of the pupilometer.

In preferred embodiments, the instrument control software is written for analysis of the pupillary response data to detect the presence of one or more specific conditions, such as to detect the presence of either drugs or alcohol in the subject's body, or the alertness or sleepiness, i.e., the fatigue, of the subject. In this instance, the software is written to compare via numerical/statistical analysis the pupillary response test data of the subject with baseline data schedules for each condition stored in the instrument memory for correlation of the pupillary response test data with the baseline schedules to determine the presence or absence of the condition being checked for. The control software is preferably written to store the results of the comparative data analysis with the identification and response test data for that test subject. Standard statistical sampling techniques may be utilized for the production of baseline data schedules from a large population of subjects for specific conditions, and known analytical techniques utilized for correlation/comparative analysis, such as, for example, the techniques disclosed in Rothberg et al. U.S. Pat. No. 5,422,690.

Baseline data schedules for more than one condition may be stored in the control pack 11. In this instance, the pupilometer is adapted to test for such multiple conditions through software controlled comparison of the pupillary response data with each of the baseline data schedules. In such embodiments, the pupilometer software is written to either check for correlation with all the stored data conditions, or for checking such conditions as selected by the operator. In the later instance, the pupilometer includes test selection means via actuation of a control switch 24 designated for each such condition, or alternate means such as through selection with the control switches 24 of a software generated menu of choices displayed on the display screen 20; and preferably, the control software is written to accept designation of the condition(s) to be checked both prior to or after the pupillary response test is conducted and the response data collected. Alternately, the instrument is designed for automatically checking for the presence of one or more specific conditions upon completion of the pupillary response test.

With the pupilometer 10 as described herein, and for operator administered testing, the operator will power-up the pupilometer by actuation of a designated on-off control switch 24; begin software controlled sequencing for and input the test and subject identification data utilizing designated control switches; and select the tests to be conducted or conditions to be checked for. Testing of the pupillary response of eye 40 may then proceeds as generally discussed above. When the test is completed, the response data is preferably analyzed and a determination made in the control pack 11 as to the presence of the condition(s) being checked for. The results of this determination, and optionally the response data, are then displayed for communication to the operator, and stored with the response data and associated subject identification data.

In keeping with the invention, the pupilometer 10 includes display means for indicating the results of the comparative analysis, i.e., for indicating the presence or absence of the conditions checked for. In this instance, LEDs 36A and 36B are provided such that, for example, the control unit 11 will light LED 36A if the presence of drugs is detected, and LED 36B if drugs are not detected. Alternately, for example, LED 36A may be utilized to indicate the presence of drugs, and LED 36B to indicate the presence of alcohol in the subject's body, the absence of a lighted LED after completion of the data analysis indicating the absence of such conditions. Additional LEDs are provided as desired for each condition being tested, with appropriate condition specific identification markings associated with such LEDs to assist the operator in identification of the condition detected. Alternate suitable display means includes utilizing the display screen 20 for displaying the results of the test data and analysis, and the presence or absence of the conditions being checked.

In accordance with yet another aspect of the invention, the second eyepiece location 18B is preferably a non-operative or blind eyepiece through which no optical communication is available with the interior of the housing 12. In the embodiment shown, the second eyepiece 18B is closed with a solid plate 32 to block light from the interior of the housing, and to isolate the associated eye 42 from the internal response-inducing light source in the optical pack 13 of the pupilometer 10. Advantageously, after the response of the pupil of eye 40 has been checked, the pupillary response from the subject's second eye 42 may be obtained by simply inverting the pupilometer such that eye 42 is aligned with optical path "A" and repeating the test. Thus, the pupilometer 10 provides for testing of both eyes of a subject without the costs associated with either duplicate optical response inducing and measuring apparatus, or mirrors and associated hardware for optically or mechanically switching between the two eyepieces such as is utilized in Carter, U.S. Pat. No. 5,661,538. Further, isolation of the eye 42 not being tested generally precludes visual distraction of the subject during the test, and provides for additional space in the binocular-style housing provides as compared with prior known hand-held pupilometers for inclusion of the internal control unit 11.

Data transfer to and from the pupilometer 10 is provided for through one or more serial or other suitable type data transmission ports or connectors 26. Although not necessary for operation or use of the pupilometer, such a connector provides interface to external apparatus for, among other things, data download for archival purposes, software upload/update capability, to establish a communication link with calibration equipment and/or for optional remote-controlled operation of the instrument.

From the foregoing, it will be apparent that the present invention brings to the art a new and improved portable, hand-held pupilometer 10 which, while suitable for general pupilometer uses, by virtue of its compact, self-contained binocular construction, monocular operation, and integral microprocessor based control unit 11, (a) is particularly suitable for testing for specific conditions at a location remote from an office or other controlled environment, (b) is less likely to be used as a weapon as compared with prior pupilometers, and (c) although being capable of testing both of a subject's eyes, is less costly as compared with prior binocular-type pupilometers through the elimination of certain components typically used in and/or associated with prior hand-held pupilometers. Thus, the pupilometer of the present invention results in substantial benefits as compared with prior hand-held pupilometers.

I claim:

1. A self-contained hand-held pupilometer for measuring pupillary response of a test subject to light stimulus, said pupilometer comprising:

a hand-held sized binocular-type housing with two eyepiece locations laterally spaced at the back of said housing for positioning generally aligned with the subject's eyes;

one of said eyepiece locations opening into and establishing visual communication with the interior of said housing;

optical-electronic means located in said housing for (i) generating a pupillary response-inducing light stimulus, (ii) directing the light stimulus through said open eyepiece, and (iii) generating a signal indicative of the response of the pupil aligned with said open eyepiece location to said light stimulus;

microprocessor-based control means located in said housing and operably connected to said optical-electronic means for (i) controlling the operation of said optical-electronic means, (ii) receiving and processing said signal, and (iii) storing pupillary response data generated therefrom; and a battery located in the housing connected to supply power to said optical-electronic means and said control storage means.

2. A pupilometer as defined in claim 1 in which the other of said eyepiece locations is closed to prevent visual communication with the interior of said housing.

3. A pupilometer as defined in claim 1 further comprising flexible eyecup means surrounding said eyepiece locations and extending rearwardly from the back of said housing for assisting with alignment of the subject's eyes with said eyepiece locations and for generally isolating the subject's eyes from outside light.

4. A pupilometer as defined in claim 1 further comprising a data-communication port operably connected to said control means for data communication with external apparatus.

5. A pupilometer as defined in claim 1 further comprising a first switch positioned for actuation by one of the subject's fingers or thumb of one of the subject's hands to initiate testing of the subject's pupillary response to said light stimulus.

6. A pupilometer as defined in claim 5 further comprising a second switch positioned for actuation by one of the subject's fingers or thumb of the other of the subject's hands to initiate testing when both switches are actuated.

7. A pupilometer as defined in claim 1 in which said control means is further adapted for comparison of the response data with a baseline data schedule stored in the instrument and for the determination of the presence and absence of a specific condition in the test subject according to the baseline data schedule, said pupilometer further comprising means located in said housing and connected to said control means for indicating the presence and absence of said condition in the test subject.

8. A pupilometer as defined in claim 7 in which said indicating means includes light emitting diodes.

9. A pupilometer as defined in claim 1 in which said control means is further adapted to receive and store test identification data, said pupilometer further comprising means located in said housing and operably connected to said control means for inputting said test identification data.

10. A method for measuring pupillary response of a test subject to light stimulus, said method comprising the steps of:

providing a self-contained hand-held pupilometer comprising a hand-held sized binocular-type housing with two laterally spaced eyepiece locations, one of said eyepiece locations opening into and establishing visual communication with the interior of said housing;

aligning said eyepiece locations generally with the subject's eyes;

measuring the response of the one pupil associate with said one eyepiece location to a light stimulus projected therethrough;

flipping the pupilometer 180 degrees such that the subject's other pupil is generally aligned with said one eyepiece location; and measuring the response of said other pupil to a light stimulus projected through said one eyepiece location.

11. A method as defined in claim 10 further comprising the steps of providing a manually operable switch located in said housing, said switch being operably connected for initiating said measuring steps;

actuating said switch with one of the subject's fingers and thumb of one of the subject's hands to initiate said measuring step associated with said one pupil; and actuating said switch with one of the subject's fingers and thumb of the subject's other hand to initiate said measuring step associated with said other pupil.

12. A method for measuring pupillary response of a test subject to light stimulus, said method comprising the steps of:

providing a hand-held pupilometer comprising (i) a hand-held sized housing with two laterally spaced eyepiece locations and (ii) means located in said housing for generating a signal indicative of the subject's pupillary response to a light stimulus, one of said eyepiece locations establishing visual communication with said optical-electronic generating means, the other of said eyepiece locations being permanently isolated to prevent visual communication with said generating means;

aligning said eyepiece locations generally with the; subject's eyes; and measuring the response of the one pupil associate with said one eyepiece location to a light stimulus projected therethrough;

said pupilometer being capable of measuring the response of the subject's other pupil by: (i) flipping the pupilometer 180 degrees such that the subjects's other pupil is generally aligned with said one eyepiece location, and (ii) measuring the response of said other pupil to a light stimulus projected through said one eyepiece location.

13. A method as defined in claim 12 further comprising the steps of providing manually operable switch means located in said housing, said switch being operably connected for initiating said measuring steps; and actuating said switch means with one of the subject's fingers and thumb of one of the subject's hands to initiate said measuring step associated with said one pupil;

said switch means being positioned for actuation with one of the subject's fingers and thumb of the subject's other hand to initiate said measuring step associated with said other pupil.

* * * * *